United States Patent [19]

Umezawa et al.

[11] Patent Number: 4,859,593

[45] Date of Patent: Aug. 22, 1989

[54] NEW PHYSIOLOGICALLY ACTIVE SUBSTANCE, ARPHAMENINE AND PRODUCTION THEREOF

[75] Inventors: Hamao Umezawa, Tokyo; Takaaki Aoyagi, Fujisawa; Tomio Takeuchi, Tokyo; Masa Hamada, Tokyo; Masaaki Ishizuka, Tokyo, all of Japan

[73] Assignee: Zaidin Hojin Biseibutsu Kagaku Kenky Kai, Tokyo, Japan

[21] Appl. No.: 809,215

[22] Filed: Dec. 16, 1985

Related U.S. Application Data

[63] Continuation of Ser. No. 500,396, Jun. 2, 1983.

[30] Foreign Application Priority Data

Jun. 7, 1982 [JP] Japan .................................. 57-96276

[51] Int. Cl.$^4$ ............................................. C12P 13/00
[52] U.S. Cl. ..................................... 435/128; 435/822
[58] Field of Search .................... 435/128, 822, 252.1; 514/565

[56] References Cited

PUBLICATIONS

Sykes et al., "Monocyclic $\beta$-Lactam Antibiotics produced by Bacteria", Nature, vol. 291, pp. 489–491, 1981.
Umezawa et al., Chemical Abstracts, vol. 100, No. 175262, 1983.

Primary Examiner—Charles F. Warren
Assistant Examiner—Gail F. Knox
Attorney, Agent, or Firm—Larson and Taylor

[57] ABSTRACT

New physiologically active substances, arphamenine A and arphamenine B which are generically termed arphamenine are produced from a new microorganism, BMG361-CF4 strain identified as FERM P-6521 or FERM BP-286 or ATCC No. 39373. Arphamenine is useful as a host defence stimulator having an activity to enhance cell-mediated immunity, and also as an antitumor agent.

2 Claims, 6 Drawing Sheets

NEW PHYSIOLOGICALLY ACTIVE SUBSTANCE, ARPHAMENINE AND PRODUCTION THEREOF

This is a continuation of application Ser. No. 500,396 filed June 2, 1983, (now U.S. Patent No. 4,596,698).

SUMMARY OF THE INVENTION

This invention relates to new physiologically active compounds, named arphamenine A and arphamenine B, having an activity inhibitory to an enzyme, aminopeptidase B and having immunopotentiating properties and anti-tumor properties. This invention also relates to the process for the production of arphamenine and to uses thereof as the host defence stimulator and as the anti-tumor agent in living animals and humans.

BACKGROUND OF THE INVENTION

Many strains of the bacteria produce therapeutically useful substances, such as antibiotics. Some substances useful as the host defence stimulator or immunopotentiator or as the anti-tumor agent are known, but there remains a need for a more effective agents useful for therapeutic treatment of various diseases in living animals, including humans.

An object of this invention is to provide new compounds which are useful as the immunopotentiator and/or the anti-tumor agent. A further object of this invention is to provide a process for the fermentative production of these new compounds. Other objects will be clear from the following descriptions.

We have made extensive our research in an attempt to produce and obtain new physiologically active compounds. As a result, we have now found that when a new strain of the genus Chromobacterium which was isolated from a soil sample collected at Poropinai on the shore of Lake Shikotsu, Hokkaido, Japan and which was alloted a laboratory designation, BMG361-CF4 strain, is cultivated in a culture medium, there are produced and accumulated in the culture new substances which show the activities inhibitory to aminopeptidase B. We have succeeded in isolating these new substances from the culture and purifying them. From the chemical, physical and biological studies of these isolated substances, it has been confirmed that each of these isolated substances is a new compound which is less toxic and which is distinguishable from any of the known compounds. Thus, we have denominated these two new compounds as arphamenine A and arphamenine B, respectively. Arphamenines A and B have the chemical structures and physico-chemical properties as described later.

DETAILED DESCRIPTION OF THE INVENTION

According to a first aspect of this invention, therefore, there is provided as the new compound, arphamenine which is selected from arphamenine A and arphamenine B and which is represented by the following general formula

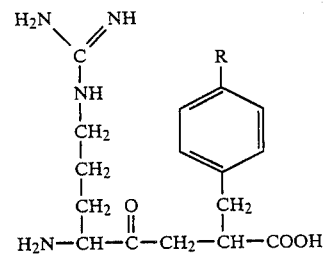

wherein R denotes a hydrogen atom for arphamenine A and R denotes a hydroxyl group for arphamenine B, or a pharmaceutically acceptable salt of the arphamenine.

Arphamenine A and arphamenine B both have an antiaminopeptidase B activity and are represented by the following chemical structures, respectively.

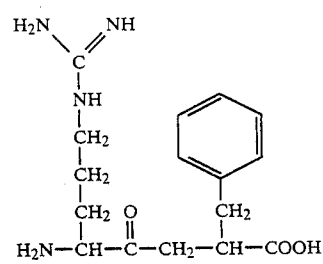

Arphamenine A

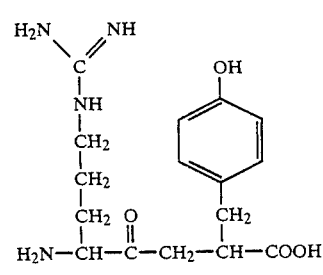

Arphamenine B

Herein, by the term "arphamenine" is meant arphamenine A or arphamenine B or a mixture of them, unless otherwise stated. This invention embraces arphamenine A and arphamenine B, either alone or in a mixture of them, which may be present in a dilute solution, as a crude concentrate, as a crude solid or as a purified solid.

We have further conducted our research on utilities of arphamenine as a medicine, and we have now found that arphamenine exhibits not only an activity to enhance the cell-mediated immune response in living animals but also an activity to inhibit the tumors in living animals. In these circumstances, arphamenine is promising to be useful in many and various therapeutic applications, by utilizing the biological properties of arphamenine, for example, in the field of immunological treatment of tumors.

We have tested whether arphamenine is inhibitory to the enzymatic activity of an aminopeptidase B to degrade arginine-B-naphthylamide, and it has been revealed that arphamenne has the anti-aminopeptidase B activity, as demonstrated by the experiments given hereinafter.

Arphamenines A and B both are obtained in the form of colorless powders, generally by cultivating an arphamenine-producing bacterium in a culture medium, treating the resulting culture broth filtrate with an adsorbent to adsorb the arphamenine, extracting the adsorbent with an aqueous organic solvent, fractionating the organic extract chromatographically on CM-Sephadex or in any suitable way and then concentrating the active fractions containing arphamenine, followed by chromatographic isolation of arphamenines A and B.

Physico-chemical properties of arphamenine are described below.

Arphamenine A is a compound which is in the form of a colorless powder and shows a melting point of 117° C. to 119° C. The molecular weight is 320 as determined by mass spectrometry. Arphamenine A hydrochloride gives an elemental analysis: C 53.45%, H 7.11%, N 14.91%, O 14.20%, Cl 10.49%, indicating the molecular formula $C_{16}H_{24}N_4O_3 \cdot HCL$. The ultraviolet absorption spectrum of arphamenine A in water (100 mcg/ml) shows an absorption peak at $\lambda_{max}$ 257 nm ($\epsilon$180), as shown in FIG. 1 of the accompanying drawings. The infrared absorption spectrum of arphamenine A pelleted in potassium bromide shows the characteristic absorption bands at 3370, 3170, 2950, 1730, 1670, 1560, 1460, 1410, 320, 1190, 1110, 760 and 710 cm$^{-1}$, as shown in FIG. 2 of the accompanying drawings. In the proton nuclear magnetic resonance absorption spectrum ($^1$H-NMR.) of arphamenine A (in deutro-water, $\delta$, 100 MHz), there are given peaks at 2.04–2.33 (CH$_2$), 2.35–2.72 (CH$_2$), 3.34–3.69 (CH$_2 \times 2$), 3.69–3.84 (CH, CH$_2$), 4.83 (CH), and 7.82–8.00 (C$_6$H$_5$), as shown in FIG. 3 of the accompanying drawings.

Arphamenine B is a compound which is in the form of a colorless powder and shows a melting point of 118° C. to 120° C. The molecular weight is 336 as determined by mass spectrometry. Arphamenine B hydrochloride hydrate gives an elemental analysis: C 49.30%, H 6.88%, N 13.77%, O 20.82% and Cl 8.73%, indicating the molecular formula $C_{16}H_{24}N_4O_4 \cdot HCL \cdot H_2O$. The ultraviolet absorption spectrum of arphamenine B in water (100 mcg/ml) shows absorption peaks at $\lambda$max 275 nm ($\epsilon$1040) and $\lambda$max 222 nm ($\epsilon$5500) as shown in FIG. 4 of the accompanying drawings. The infrared absorption spectrum of arphamenine B pelleted in potassium bromide shows the characteristic absorption bands at 3370, 3180, 2960, 1730, 1670, 1560, 1520, 1460, 1420, 1330, 1250, 1180, 1110 and 840 c$^{-1}$, as shown in FIG. 5 of the accompanying drawings. In the proton nuclear magnetic resonance absorption spectrum ($^1$H-NMR) of arphamenine B (in deutro-water, $\delta$100 MHz), there are given peaks at 1.87–2.30 (CH$_2$), 2.30–2.62 (CH$_2$), 3.14–3.54 (CH$_2 \times 2$), 3.54–3.78 (CH, CH$_2$), 4.75 (CH), 7.30–7.67 (C$_6$H$_4$) ppm, as shown in FIG. 6 of the accompanying drawings.

With reference to the accompanying drawings.

Figure 1:
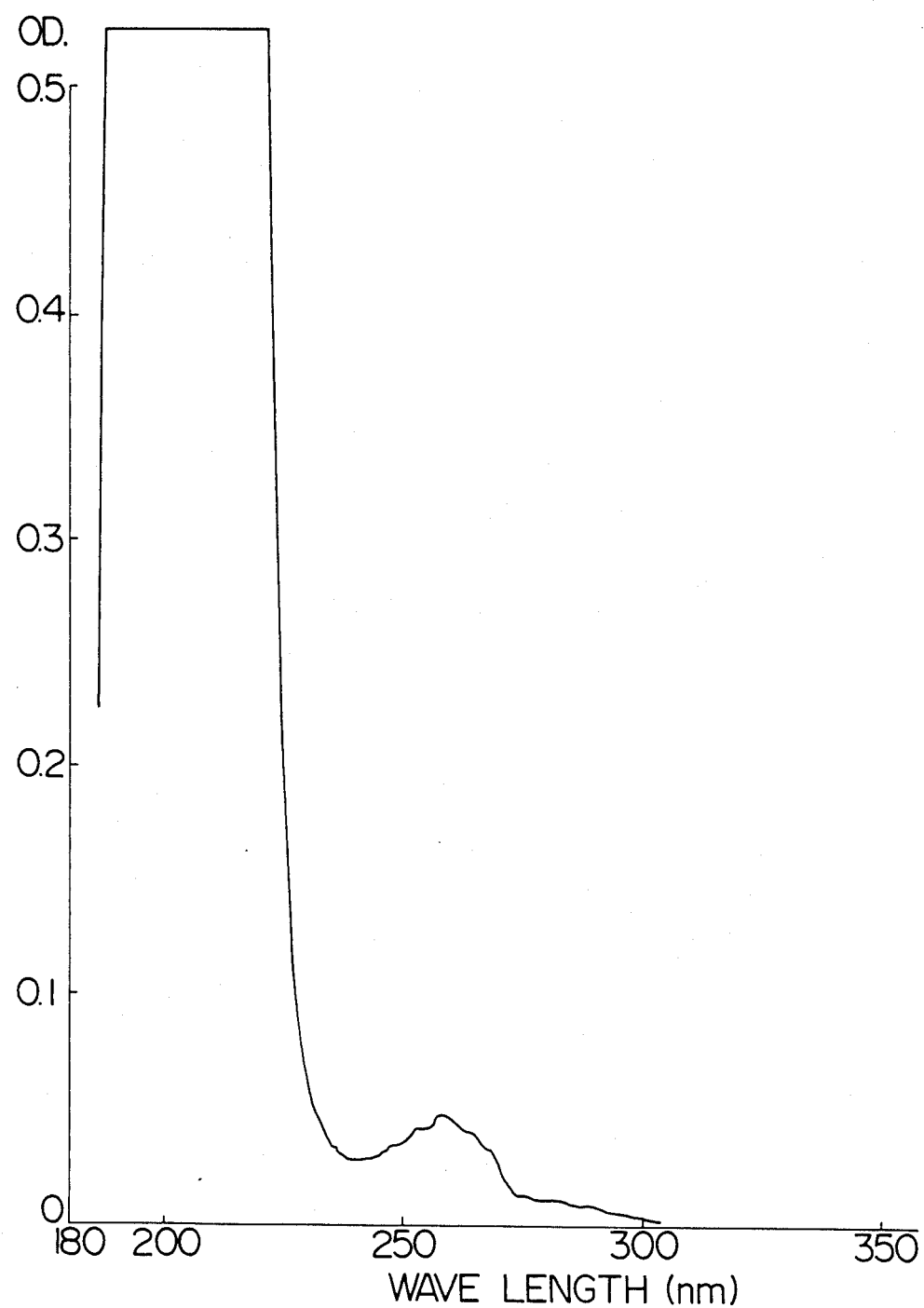
FIG. 1 shows the ultraviolet absorption spectrum of arphamenine A according to this invention.
Figure 2:
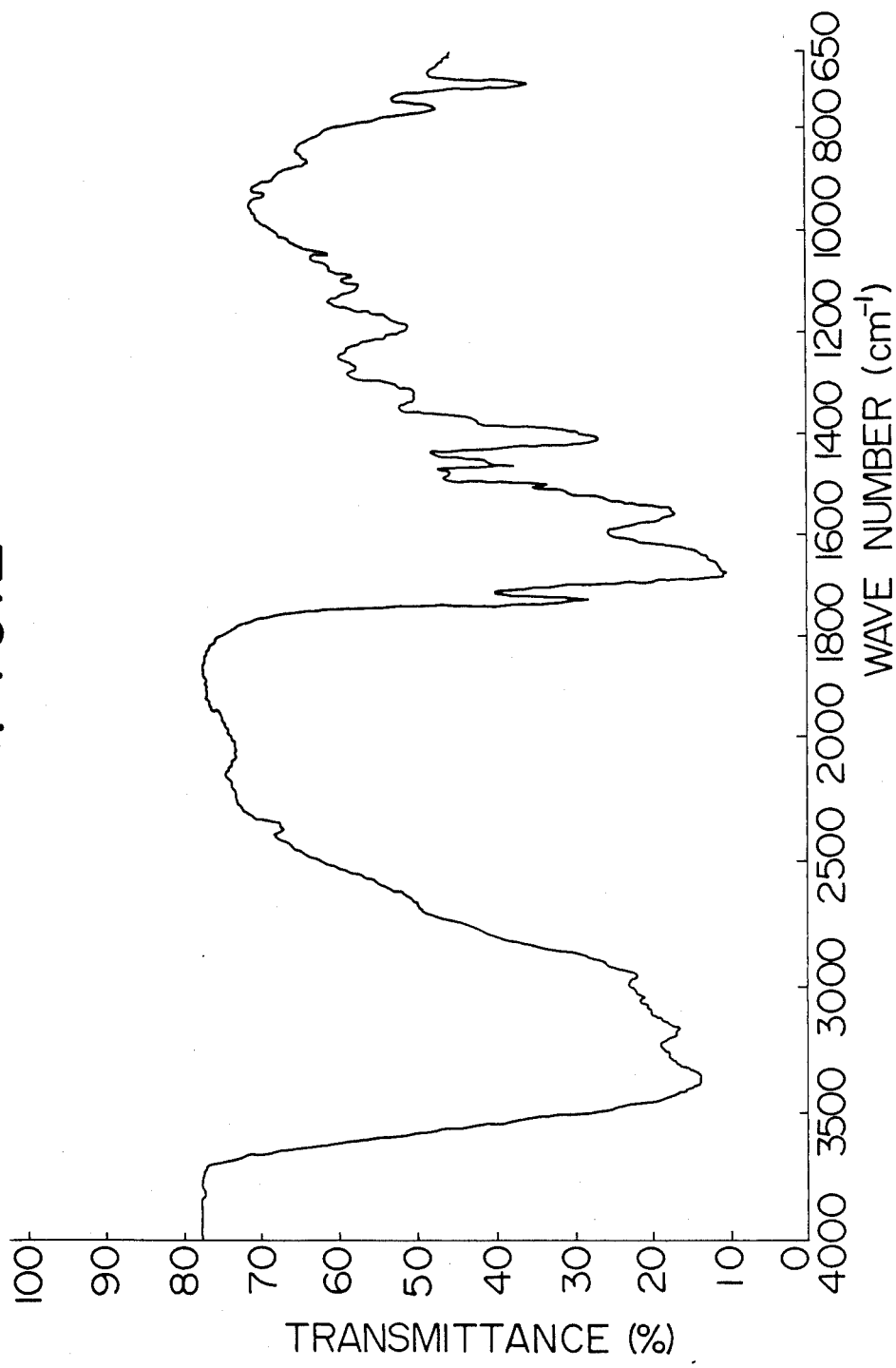
FIG. 2 shows the infrared absorption spectrum of arphamenine A.
Figure 3:
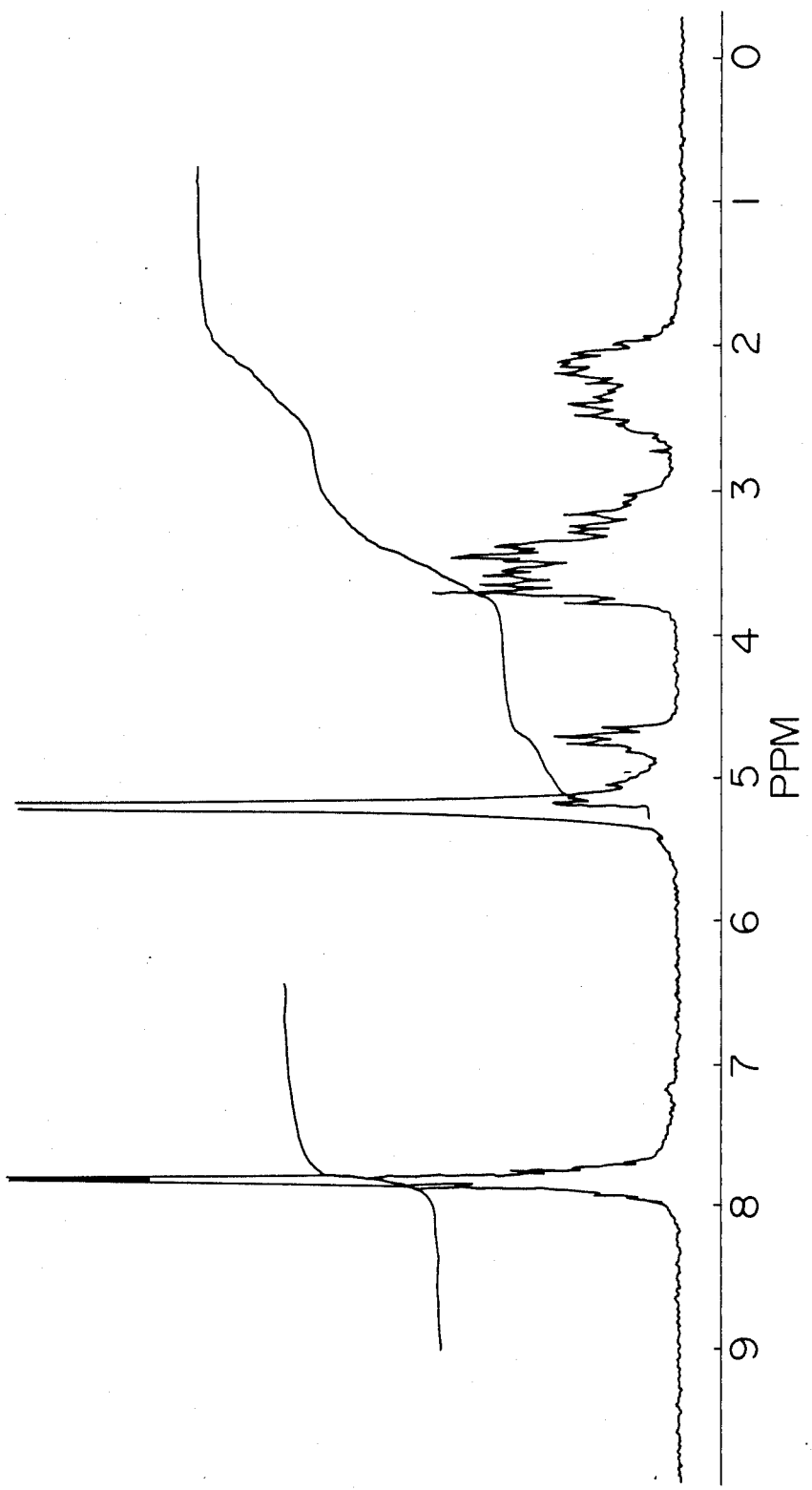

FIG. 3 gives the nuclear magnetic resonance absorption spectrum of arphamenine A.

Figure 4:
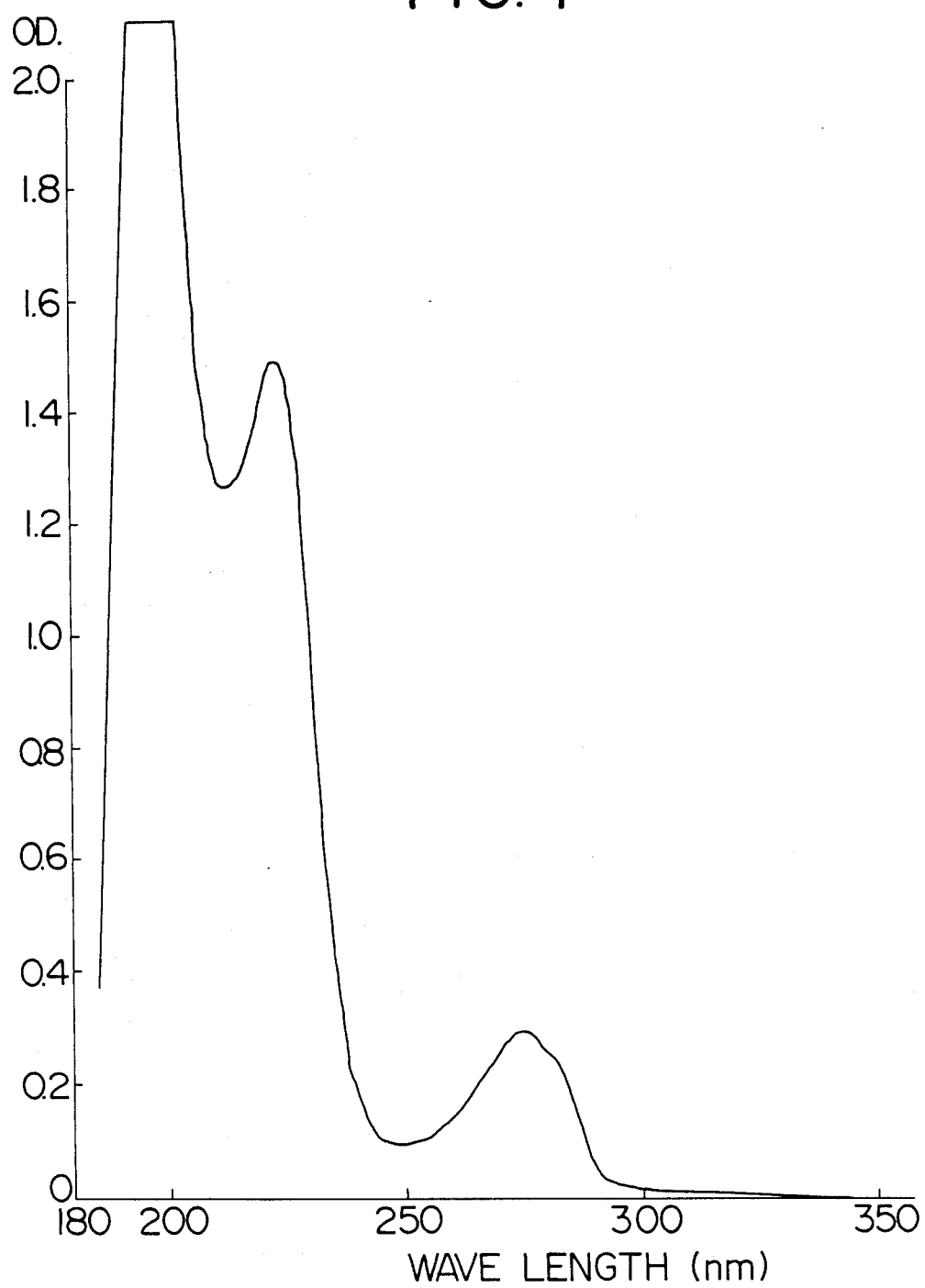

FIG. 4 shows the ultraviolet absorption spectrum of arphamenine B claimed in this invention.

Figure 5:
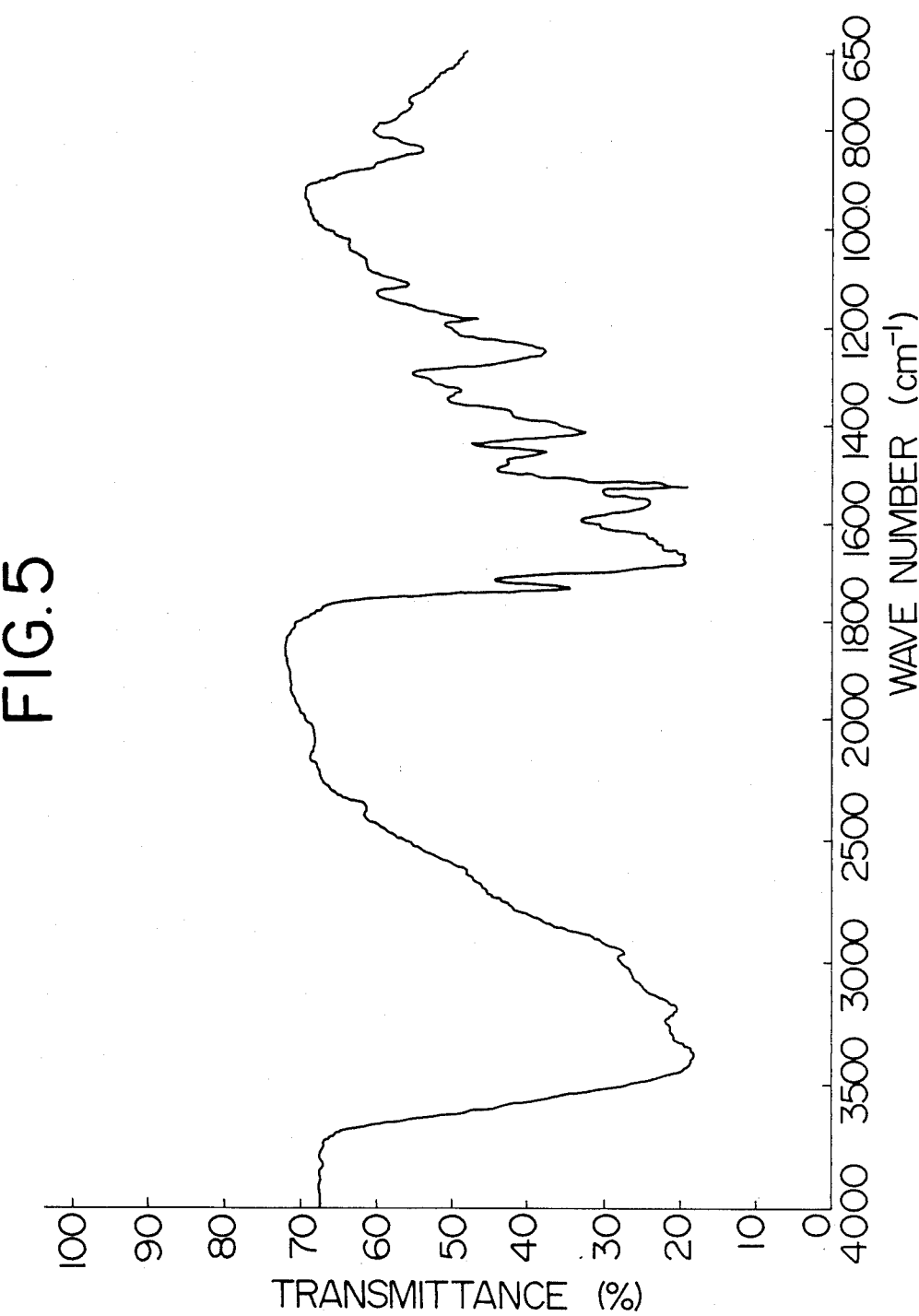

FIG. 5 illustrates the infrared absorption spectrum of arphamenine B.

Figure 6:
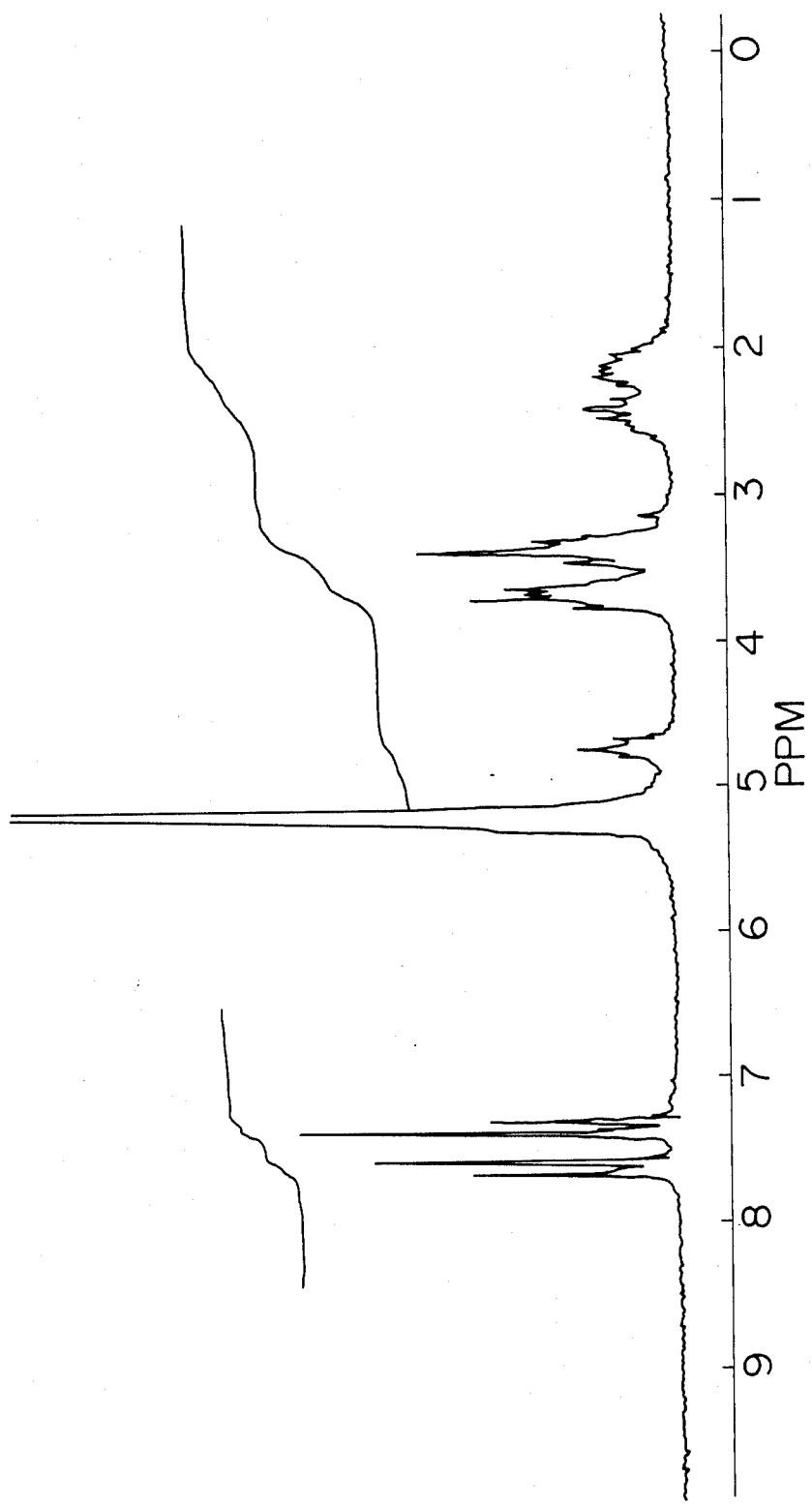

FIG. 6 shows the nuclear magnetic resonance absorption spectrum of arphamenine B.

According to a second aspect of this invention, there is provided a process for the production of an arphamenine, which comprises cultivating an arphamenine-producing strain of the genus Chromobacterium in a culture medium containing assimilable carbon and nitrogen sources for a sufficient time to produce and accumulate arphamenine in the culture medium. This process may include further the step of recovering the arphamenine from the culture obtained.

According to an embodiment of this second aspect invention, there is provided a process of producing arphamenine A which comprises cultivating an arphamenine A-producing strain of the genus Chromobacterium in a culture medium containing assimilable carbon and nitrogen sources for a sufficient time to produce and accumulate arphamenine A in the culture. According to an another embodiment, there is provided a process of producing arphamenine B, which comprises cultivating an arphamenine B-producing strain of the genus Chromobacterium in a culture medium containing assimilable carbon and nitrogen sources for a sufficient time to produce and accumulate arphamenine B in the culture. The process of the second aspect invention includes further the step of recovering from the culture arphamenine A and arphamenine B, either alone separately or in the form of a mixture or as a crude product or a purified product.

In the process of this invention, the arphamenine-producing strain means such a microorganism capable of producing arphamenine A or B or both arphamenines. An example of the microorganism is *Chromobacterium violaceum* BMG361-CF4, a strain that was isolated by the inventors of this invention from soil collected at Poropinai on the shore of Lake Shikotsu, Hokkaido, Japan. This strain has been deposited on and since May 4, 1982 in the "Fermentation Research Institute", Agency of Industrial Science and Technology, Ministry of International Trade and Industry of Japan under deposit number FERM P-6521, and deposited under FERM BP-286 according to Budapest Treaty, and also deposited in the American Type Culture Collection, 12301 Parklawn Drive, Rockville, Md. 20832U.S.A., under ATCC number 39373.

The microbiological characteristics of the abovementioned BMG361-CF4 strain will be detailed below.

(a)

Morphological characteristics (1) Shape and size of the cell: Rod; about 0.8 to 1.0 microns $\times$ 2.0 to 4.0 microns (2) Pleomorphism: Non-pleomorphic (3) Motility/flagellation: Motile/polar and lateral flagella (4) Sporogenicity: Non-sporulating (5) Gram's stain : Negative (b)

Culture characteristics on various culture media (incubated at 27° C., excepting 20° C. and 30° C. for bouillon gelatin stab culture)

(1) Bouillon agar plate culture

Colonies grown were somewhat elevated semispherically, and their margins were smooth and circular. The growth surfaces smoothed and glistened. After about 17 hours of incubation, the colonies were translucent, but gradually became opaque and presented a rubbery appearance. Around the second day of incubation, the colonies turned purple, but produced no diffusible pigments.

(2) Bouillon agar slant culture

Colonies grew uniformly along the lines of inoculation. The growth surfaces were sooth and lustrous, and the margins smoothed. Around the second day of incubation, colonies at the bottom of the slanting agar surface developed a purple color, but no soluble pigments were observed.

(3) Bouillon liquid culture

Around the second day of incubation, purple annular colonies were formed on the surface of the medium. After about 40 hours of incubation, the number of cells at the bottom of the test tube increased. The cells turned purple around the third day of incubation.

(4) Bouillon gelatin stab culture.

When the incubation temperature was 30° C., cells grew along the line of stab. Around the third day of incubation, the medium liquefied, and the area of liquefaction had a tubular form. In the case of incubation at 20° C., liquefaction of the medium started on the sixth day of incubation.

(5) BCP milk culture

After 3 days of incubation, BCP turned blue, and the medium was coagulated. On the 5th day of incubation, the coagulation was completed, and immediately, peptonization began. Peptonization was completed in about 2 weeks.

(c)

Physiological characteristics (all observed at an incubation temperature of 27° C., unless otherwise specified)

(1) Reduction of nitrates: Formation of nitrites from nitrates (2) Denitrification (method of Komagata et al., edited by Takeharu Hasegawa: "Classification and Identification of Microorganisms", page 223, Tokyo University Publisher, 1975): Positive, no development of gases (3) MR test: Positive (4) VP test: Negative (5) Production of indole: Negative (6) Production of hydrogen sulfide (TSI Agar Medium, a product of Eiken Company, Japan): Negative (7) Hydrolysis of starch: Negative (8) Utilization of citric acid: Positive on a Koser medium and a Christensen medium (9) Utilization of inorganic nitrogen source (ammonium sulfate, and sodium glutamate): Utilized each of the inorganic nitrogen sources

(10) Production of pigment (King A and B Media, products of Eiken Company): Tiny amounts of a yellow soluble pigment formed on each medium

(11) Urease (Uria Medium, a product of Eiken Company): Negative

(12) Oxidase: Positive

(13) Catalase: Positive

(14) Temperature and pH ranges for growth

Grew at at 12 to 37° C., optimally at about 27 to 30° C. Grew at a pH of 5.0 to 8.6, optimally at pH of 6.0 to 7.8.

(15) Oxygen demand: Aerobic (facultative anaerobic)

(16) 0-F test (according to the Hugh & Leifson method): Fermentative

(17) Production of acids and gases from saccharides (in a Hugh & Leifson culture medium): Acids were produced from D-glucose, D-fructose and trehalose. No acids were produced from the following 19 saccharides: L-arabinose, D-xylose, D-mannose, D-galactose, maltose, sucrose, lactose, D-sorbitol, D-mannitol, inositol, glycerin, starch, adonitol, cellobiose, dulcitol, inulin, melibiose, melezitose, and raffinose. None of the saccharides produced gases.

(18) Hydrolysis of casein: The microorganism was streak-cultured in a casein agar plate (pH 7.4) which had been prepared by adding sterilized skim milk to a bouillon agar to a concentration of 5%, and solidifying the mixture. After 24 hours of incubation, casein was digested, and its hydrolysis was completed on the 8th day of incubation.

(19) Visible spectrum measurement on purple pigment. The purple-colored cells grown in the bouillon agar slant were extracted with ethanol, and the extract was measured for its visible spectrum. Maximum absorption was observed at 573 nm, and minimum absorption at 430 nm. When the pigment was dissolved in ethanol containing 10% sulfuric acid, it gave a green solution which showed a maximum absorption at 693 nm. This fact revealed the purple pigment to be a violacein pigment (see Bergey's Manual of Determinative Bacteriology, 8th edition, p. 354).

Summarizing the above-mentioned characteristics of the BMG361-CF4 strain, it is noted that BMG361-CF4 strain is a gram-negative, facultative anaerobic bacillus having polar and lateral flagella. Its growths (colonies) contained a purple pigment, which was identified as violacein on measurement of its visible spectrum. On the basis of these properties of the BMG361-CF4 strain, this strain was compared with the known ones with reference to Bergey's Manual of Determinative Bacteriology 8th edition, revealing that the BMG361-CF4 strain belongs to the genus Chromobacterium. The genus Chromobacterium includes the two species, *C. violaceum* and *C. lividum*. BMG361-CF4 strain possessed the microbiological properties most closely resembling to those of the former species. In detail, BMG361-CF4 strain was clearly distinguished from *C. lividum* in terms of growth at 37° C., patterns of acid formation from saccharides (acid production from trehalose; no acid production from arabinose or xylose), and hydrolysis of casein, etc. Accordingly, the BMG361-CF4 strain was identified as *Chromobacterium violaceum* BMG361-CF4.

The process of this invention will be described in detail below.

In the process of this invention, arphamenine can be produced by cultivation of an arphamenine-producing strain of the genus Chromobacterium, for example, *Chromobacterium violaceum* BMG361-SF4 strain (identified as FERM P-6521 or FERM BP-286 or ATCC 39373).

In carrying out the process of this invention, an amount of an arphamenine-producing strain is inoculated to a suitable culture medium therefor comprising assimilable carbon and nitrogen sources and is then incubated under aerobic conditions, preferably under submerged aerobic conditions, so that arphamenine is produced and accumulated in the culture broth. Generally, nutrient constituents of the culture media commonly employed for cultivation of bacteria can be used for the purpose of this invention. For instance, commercially available glycerin, glucose, lactose, sucrose, starch, maltose, molasses and other carbohydrates, fat and oil and the like are useful as the carbon source. Commercially available peptone, meat extract, corn steep liquor, cotton seed meal, peanut meal, soybean meal, corn gluten meal, fish meal, yeast extract, N-Z amine, casein, sodium nitrate, ammonium nitrate, ammonium sulfate and the like may be useful as the nitrogen source. In addition, sodium chloride, phosphates, calcium carbonate, magnesium sulfate and other inorganic salts can be employed for the salt-additive in the culture medium. Other metal salts and various heavy metal salts may also be added in trace quantities, if required, as long as they are utilized by the arphamenine-producing strain and are not detrimental to the production of arphamenine. Any of the nutrient materials which are known for cultivation of bacteria may be employed in the process of this invention, as far as it is assimilable by the arphamenine-producing strain for the production of arphamenine. Amongst the preferred components of the culture media, particularly glycerin, soluble starch and the like are preferred as the carbon source; and soybean meal, fish meal, corn gluten meal and the like are preferred as the nitrogen source. A culture medium comprising 1.5% glycerin, 1.5% soluble starch, 0.5% Prorich, 1.5% fish meal, 0.2% calcium carbonate, or a culture medium comprising 3% soluble starch, 0.5% Prorich, 1.2% corn gluten meal, 0.2% calcium carbonate is preferred for use.

For the production of arphamenine on a large scale, liquid cultivation is preferred. Any temperature at which the arphamenine-producing strain is able to grow and produce arphamenine can be employed for the cultivation, but a preferred incubation temperature is in a range of 25° C. ~35° C., especially at 27° C. The cultivation is continued for a period of time sufficient to produce and accumulate a sufficient amount of arphamenine in the culture medium.

For instance, the production and accumulation of arphamenine was observed at the end of 8 hours to 52 hours of incubation when a culture medium comprising 3% soluble starch, 0.5% Prorich, 1.2% corn gluten meal and 0.2% calcium carbonate was prepared and sterilized, followed by inoculation with a loopful quantity of the arphamenine-producing strain as harvested from its slant culture and by shake-cultivation at 27° C. under aerobic conditions. Arphamenine can be produced satisfactorily by cultivation in a fermentation-tank as well as by shake-cultivation. For example, 300 l of a culture medium was placed in a fermentation tank of 570 l capacity, sterilized and inoculated with the arphamenine-producing strain, followed by the cultivation with aeration of sterilized air at 300 l per minute and under agitation at 190 r.p.m., when the production and accumulation of arphamenine reached a maximum at the end of 23 hours of incubation.

Tracing of arphamenine which was made during the course of cultivation of the arphamenine-producing strain, as well as during the course of recovery and purification of arphamenine was conducted by determining the antiaminopeptidase B potency of arphamenine according to the following methods.

Thus, the assay of arphamenine for its anti-aminopeptidase B potency was made according to a modification of the method of Hoppusu et al. as described in the "Archives of Biochemistry and Biophysics" 114, 557 (1966) by V.K. Hoppusu, K.K. Makinen & G.G. Glenner. In detail, 0.5 ml of 0.1 M tris-hydrochloride buffer solution (pH 7.0) and 0.25 ml of a solution containing an arphamenine specimen were added to 0.25 ml of a substrate solution containing 0.002 M arginine-$\beta$-naphthylamide. The mixed solution so obtained was heated at 37° C. for 3 minutes. To the heated solution was added 5 $\mu$l of a solution of an aminopeptidase B which had been purified with DEAE-Cellulose according to the enzyme-purification technique of Hoppusu et al. The resulting mixture was reacted for 30 minutes at 37° C., and the resultant reaction mixture was admixed with 1 ml of 1.0 M acetate buffer solution (pH 4.2) containing Fast Garnet GBC (o-aminoazotoluene, diazonium salt) at a concentration of 1 mg/ml and a surfactant "Tween" 20 at a concentration of 10% to stop the enzyme reaction. After allowing the resulting mixture to stand at ambient temperature for 15 minutes, absorbance (a) at 525 nm of the reaction solution was measured. On the other hand, adsorbance (b) at 525 nm of a control reaction solution obtained from the blank test using the buffer solution containing no arphamenine was measured. Percent of inhibition to the aminopeptidase B was calculated from the equation $[(b-a)/b] \times 100$. In accordance with this assay method, the colorless, pure product of arphamenine A had a potency such that its $IC_{50}$, namely the dose of giving 50% inhibition to the aminopeptidase B amounted to 0.005 mcg/ml, and the colorless, pure product of arphamenine B had a potency such that its $IC_{50}$ to said peptidase amounted to 0.002 mcg/ml.

For recovery of arphamenine from the culture of the arphemenine-producing microorganism, the culture broth after completion of the incubation may be processed in various ways. Arphamenine exists in the culture broth and cells of the arphamenine-producing microorganism after the incubation. Arphamenine can be recovered from the culture broth in good yields by treating a filtrate of the culture broth with an adsorbent and desorbing the arphamenine from the adsorbent containing the adsorbate. Examples of the available adsorbent include organic adsorbents such as "Amberlite" XAD-4 and "Diaion" HP-20, ion-exchange resins, as well as inorganic adsorbents such as active carbon, alumina and silica gel. For example, arphamenine can be adsorbed to "Amberlite " XAD-4 resin and eluted therefrom with aqueous acetone. For instance, the recovery of arphamenine from the culture broth may be achieved using a suitable column of Amberlite XAD-4 resin amounting to one-tenth of the volume of the culture broth filtrate, in such a manner that the culture broth filtrate containing arphamenine is passed through the Amberlite XAD-4 column, this column is then washed with water and subsequently eluted with such a volume of 50% aqueous acetone which amounts to 2-folds to 4-folds the volume of the Amberlite XAD-4 resin in the column. In this way, 70% or more of the quantity of arphamenine which was initially contained in the culture broth filtrate can be eluted out into the eluate of 50% aqueous acetone. This eluate can be concentrated to dryness under reduced pressure to afford a crude powder of arphamenine.

Purification of a crude powder of arphamenine can be done chromatographically using an ion-exchanger. For tis purpose, a column chromatography on CM-Sephadex (products of Sephadex Fine Chemical Col Co., Sweden) is especially effective. For isolation of arphamenine A from arphamenine B, it is especially effective to subject a mixture of arphamenines A and B to a column chromatography on CM-Sephadex and then elute the CM-Sephadex column with aqueous sodium chloride according to the gradient elution method. For instance, an efficient method of recovering and isolating the arphamenines may comprises treating the culture broth filtrate with a column of Amberlite XAD-4 resin for the adsorption of arphamenine, eluting the Amberlite column with aqueous acetone, concentrating the active fractions of the aqueous acetone eluate to dryness under reduced pressure, subjecting the crude powder of arphamenine so obtained to a column chromatography on CM-Sephadex, eluting the CM-Sephadex column with an aqueous solution of a salt such as an alkali metal chloride, e.g. sodium chloride, collecting the eluate in such separate fractions so as to afford the active fractions containing arphamenine A and the active fractions containing arphamenine B, and then finally recovering arphamenines A and B separately from the respective active fractions.

Final purification of the arphamenines so isolated may be achieved by desalting them with Sephadex LH-20 (a product of Sephadex Fine Chemical Co., Sweden).

We have further conducted research on pharmacological properties of arphamenine, and as a result we have now found that arphamenine exhibits an activity to stimulate the immune response in living animal by enhancing the cell-mediated immunity, as well as an activity to inhibit the growth of tumors in living animal.

The biological activities of both the arphamenines A and B are described below, with reference to the following Test Examples.

Test Example 1

Effect of arphamenine on cell-mediated immunity in normal mice

Effect of arphamenines A and B on the cell-mediated immunity was tested according to a known Delayed Type Hypersensitivity (D.T.H.) technique (see P. H. Lagrange, G. B. Mackaness and T. E. Miller: "J. Exp. Med.", 139, 1529 1539 (1974)) using mice immunized with sheep red blood cells (SRBC) as the antigen inoculated to the footpad of the mice.

Thus, $10^8$ SRBC suspended in 0.05 ml of physiological saline was inoculated by subcutaneous injection to the one side of hind footpad of $CDF_1$ mice (5 mice per group, female, 8-weeks old) to make immunization. At the time of this immunization, an aqueous solution containing 5 mg/kg, 0.5 mg/kg, 0.05 mg/kg or 0.005 mg/kg of arphamenine A or B was administered orally at a single dose to each test mice. 4 Days after the immunization, $10^8$ SRBC in 0.05 ml of physiological saline was injected subcutaneously into the other side of the hind footpad of the test mice for elicitation of D.T.H. response. 24 Hours after the eliciting injection, the thickness (in mm) of the hind footpad having received the eliciting injection of SRBC was measured with calipers. At the same time, the thickness of the other side of the footpad which had not received the eliciting injection of SRBC was also measured in each mouse. The increase of footpad thickness (the swelling degree) was calculated by the following equation:

Increase of footpad thickness = (size of thickness of footpad having received the eliciting injection) −(size of thickness of footpad having not received the eliciting injection)

The effect of arphamenine on the DTH response was evaluated by the following equation:

$$T/C\ (\%) = \frac{\text{Mean value }(T)\text{ of the increase of footpad thickness in mice treated with arphamenine}}{\text{Mean value }(C)\text{ of the increase of footpad thickness in mice untreated}} \times 100$$

Therefore, the assumption was here that the value for the control mice (untreated) was evaluated to be 100%.

In this way, the cell-mediated immunity potentiating effect of the test compound was evaluated. The test results are shown in the following Tables 1 and 2:

TABLE 1

| Test compound | Dose (mg/kg) | Increased thickness of footpad (× 0.1 mm) | T/C (%) |
| --- | --- | --- | --- |
| Arphamenine A | 5 | 10.4 ± 0.77 | 125 |
| " | 0.5 | 11.5 ± 1.29 | 139 |
| " | 0.05 | 13.0 ± 0.97 | 157 |
| " | 0.005 | 11.9 ± 1.00 | 143 |
| Bestatin (Comparative) | 0.5 | 12.5 ± 1.24 | 151 |
| Control | | 8.3 ± 0.97 | 100 |

TABLE 2

| Test compound | Dose (mg/kg) | Increased thickness of footpad (× 0.1 mm) | T/C (%) |
| --- | --- | --- | --- |
| Arphamenine B | 5 | 13.7 ± 1.77 | 157 |
| " | 0.5 | 14.7 ± 1.74 | 169 |
| " | 0.05 | 14.0 ± 1.33 | 161 |
| " | 0.005 | 12.4 ± 1.40 | 143 |
| Bestatin (Comparative) | 0.5 | 13.0 ± 1.13 | 149 |
| Control | | 8.7 ± 1.48 | 100 |

Test Example 2

Effect of arphamenine on cell-mediated immunity in tumor-bearing mice (1) D.T.H. to SRBC The swelling degree on the footpad in mice was evaluated in the same way as in Test Example 1, except that the $CDF_1$ mice employed for the test previously received an intraperitoneal inoculation of $10^6$ Sarcoma 180 cells, and that arphamenine A was administered intraperitoneally once daily for 4 consecutive days, including the day of inoculation of SRBC, and two days after the administration, SRBC was given to the treated mice to elicit D.T.H. response. The test results are shown in Table 3.

TABLE 3

| Test compound | Dose (mg/kg) | Increased thickness of footpad (× 0.1 mm) | T/C (%) |
| --- | --- | --- | --- |
| Arphamenine A | 5 | 5.8 ± 1.19 | 129 |
| " | 0.5 | 6.7 ± 1.03 | 149 |
| " | 0.005 | 6.5 ± 1.29 | 144 |
| " | 0.005 | 5.9 ± 0.79 | 131 |
| Bestatin (Comparative) | 5 | 6.0 ± 0.96 | 133 |
| Control | | 4.5 ± 0.74 | 100 |

(2) D.T.H. to picryl chloride

In mice bearing Ascites Sarcoma 180 tumor, the effect of arphamenine A on D.T.H. to picryl chloride as antigen was investigated. Thus, $10^6$ cells of Ascites Sarcoma 180 were transplanted intraperitoneally into $CDF_1$ mice (12-week-old, female, 6 mice per group). The day of this transplantation was designated as Day 0. On Day 1, a shaved area (25 mm × 15 mm) of the abdomen of the mice was immunized 0.6 ml of a solution of 6% picryl chloride in ethanol which had been absorbed to a mass of cut absorbent cotton (20 mm×20 mm×2 mm in size). On Day 8, the thickness of the auricles of both ears was measured with a dial gauge to obtain a baseline value (a). Then, both auricles were elicited for the D.T.H. response with a solution of 1% picryl chloride in olive oil which had been absorbed to a mass of cut absorbent cotton (10 mm×4 mm×1 mm in size). On Day 9, the swelling degree on the elicited auricles was measured with a dial gauge to obtain a value (b). The baseline value (a) was subtracted from the value (b) to determine an increase in the thickness of the auricles (b−a) in the control group of mice (c). Separately, 0.5, 0.05 or 0.005 mg/kg of the test compound dissolved in physiological saline was orally administered to another group of CDF$_1$ mice 6 times/day for consecutive days of from Day 1 to Day 8 inclusive, and then the picryl chloride elicitation was carried out with the treated group of mice in the same way as in the control group of mice. The increase in the thickness of both auricles (b'−a') in this treated group of mice (T) was determined in the same way as in the control group of mice. The rate (T/C, %) of the increased thickness of auricles of the treated group (T) in term of that for the control group (c) was calculated from the following equation $$T/C\ (\%) = \frac{(b' - a')}{(b - a)} \times 100$$

Assumed that the value for the control group was evaluated to be 100%, the activity of the test compound to potentiate cell-mediated immunity was estimated. The test results are shown in Table 4.

TABLE 4

| Test compound | Dose (mg/kg) | Increased thickness of auricles (× 0.1 mm) | T/C (%) |
| --- | --- | --- | --- |
| Arphamenine A | 0.5 | 6.05 ± 0.97 | 136.0 |
| " | 0.05 | 7.40 ± 0.72* | 166.3 |
| " | 0.005 | 6.40 ± 0.63 | 143.8 |
| Control (Physiological saline solution) | | 4.45 ± 2.36 | 100.0 |

*P < 0.05

The above results demonstrate that a significant activity to enhance cell-mediated immunity was obtained in the group receiving 0.05 mg/kg of arphamenine A.

Test Example 3

Anti-tumor activity of arphamenine against Ehrlich Solid Tumor $3 \times 10^6$ cells of Ehrlich ascites tumor were transplanted subcutaneously into the flank of ddY mice (8-week old, female, 5 mice per group). The day of this transplantation was designated as Day 0. Then, 0.5, 0.05 or 0.005 mg/kg of the test compound dissolved in physiological saline solution was orally administered to the mice a total of 7 times on alternate days until Day 15, beginning on day 1. On day 30, the size (shorter diameter $^2$×longer diameter/2) of tumor and the weight of tumor were measured. The results in this treated group of mice were compared with those in the control group of mice to calculate tumor inhibition rate (TIR, %) according to the following equation:

$$TIR\ (\%) = \frac{C - T}{C} \times 100$$

where C denotes the size or weight of tumor in the control group, and T denotes the size or weight of tumor in the treated group.

For estimation of the anti-tumor effect of the test compound, the values of TIR (%) are shown in the following table:

TABLE 5

| Test compound | Dose (mg/kg) | Average size of tumor (mm$^3$) | TIR (%) | Average weight of tumor (g) | TIR (%) |
| --- | --- | --- | --- | --- | --- |
| Arphamenine A | 0.5 | 4467 ± 4311 | 15.8 | 2.62 ± 1.90 | 1.9 |
| " | 0.05 | 3120 ± 3584 | 41.2 | 1.66 ± 1.50 | 37.8 |
| " | 0.005 | 2378 ± 3138 | 55.2 | 1.62 ± 1.44 | 39.3 |
| Bestatin (reference compound) | 0.05 | 2089 ± 1946* | 60.6 | 1.47 ± 0.92** | 44.9 |
| Control | — | 5305 ± 2027 | 0 | 2.67 ± 0.84 | 0 |

*P < 0.1 (T-test)
**P < 0.05 (T-test)

The above results demonstrate that 0.05 and 0.005 mg/kg of arphamenine A produced a host-mediated anti-tumor effect in terms of tumor size and tumor weight. Thus, arphamenines A and B prove to potentiate the cell-mediated immunity in normal animals, modulate the cell-mediated immunity depressed by the tumor, and exhibit a host-mediated anti-tumor effect.

Acute toxicity tests in mice by intravenous injection have shown that no deaths are caused by arphamenine A in an iv. dose of 250 mg/kg or by arphamenine B in an iv. dose of 150 mg/kg. Arphamenine is hence a safe substance. As described above, arphamenines A and B of this invention each augment immunity and exhibit a host-mediated carcinostatic effect when administered singly. These new compounds are therefore useful as immunopotentiators and anti-tumor immunomodulators or as adjuvants to various chemotherapeutic agents for use in the treatment of carcinomas.

According to a third aspect of this invention, therefore, there is provided a pharmaceutical composition comprising a safe and effective amount of at least one of arphamenines A and B and a pharmaceutically acceptable salt thereof, in admixture with a pharmaceutically acceptable carrier.

According to a further aspect of this invention, there is provided a host defence stimulator for enhancing mainly the immune response in a living animal, which comprises as the active ingredient at least one of arphamenines A and B and a pharmaceutically acceptable salt thereof, in combination with a pharmaceutically acceptable carrier for the active ingredient.

This invention further provides a method for stimulating the immune response in a living animal, which comprises administering a safe and immunopotentiatingly effective amount of at least one of arphamenines A and B and a pharmaceutically acceptable salt thereof to said animal.

According to another aspect of this invention, there is further provided a method for inhibiting the growth of tumor in a living animal, which comprises administering a safe and anti-tumor effective amount of at least one of arphamenines A and B and a pharmaceutically acceptable salt thereof to said animal.

The drugs containing arphamenines A and B as active ingredients can be prepared by blending arphamenine A or B or both arphamenines or their pharmaceutically acceptable salts with conventional carriers, and if desired, further with various chemotherapeutic agents. Examples of the pharmaceutically acceptable salts of arphamenine include such salts which are formed by the reaction of the carboxyl group of arphamenine with a pharmaceutically acceptable cation, such as ammonium ion, cation of an alkali metal such as sodium and potassium, and cation of an alkaline earth metal such as calcium and magnesium (i.e., carboxylates of arphamenine). Additional examples include such acid-addition salts which are formed by the reaction of the guanidyl or amino group of arphamenine with a pharmaceutically acceptable inorganic acid such as hydrochloric acid, or an organic acid such as acetic acid.

The compounds or drugs of this invention may be administered as oral preparations, injections or rectal suppositories. Lyophilized injections can be prepared by admixing pH adjustors, buffers, stabilizers and excipients with said active ingredient compounds, and then freeze-drying the mixtures in customary manners. Injections for subcutaneous, intramuscular or intravenous administration can be prepared by admixing pH adjustors, buffers, stabilizers, isotonizers and local anesthetics with the active ingredient compounds, and then formulating the mixture by customary procedures.

For the preparation of oral solids, the active ingredient compound is admixed with excipients, if desired, together with binders, disintegrators, lubricants, colorants, taste correctives and odor correctives, whereafter the mixture are formed into tablets, coated tablets, granules, powders and capsules by customary methods.

For the preparation of oral liquids, the active ingredient compound may be admixed with taste correctives, buffers, stabilizers and odor correctives and then the mixtures are made into syrups and dry syrups by customary methods.

To prepare rectal suppositories, the active ingredient compound may be admixed with excipient, if desired, together with surfactant, and the mixture is prepared into suppositories by customary techniques. The dose of arphamenine to be administered to patients may be varied depending on symptoms of the disease, but the usual dosage of arphamenine is 0.02 to 200 mg for adult once daily. When concomitant therapy with other chemotherapeutic agents for cancer or other immunopotentiators is to be instituted, arphamenine in said dose range may be administered in association with these other drugs in their usual doses.

The production of the arphamenine will be described in more detail with reference to the following Examples. However, this invention is in no way limited to these Examples, since the physicochemical properties of arphamenine, and techniques for its production and purification clearly described by the present inventors would make it easy for anyone to modify the methods disclosed in the present specification.

Example 1

A loopful quantity of cells were harvested from a slant culture of the arphamenine-producing microorganism, Chromobacterium violaceum BMG361-CF4 (FERM P-6521 or FERM BP-286). The cells so harvested were inoculated into a culture medium containing 3% soluble starch, 0.5% Prorich, 1.2% corn gluten meal and 0.2% calcium carbonate, which culture medium had been sterilized at 120° C. for 20 minutes and dispensed in 110 ml portions in 500 ml rotary flasks. The inoculated culture medium was incubated at 27° C. and under agitation at 180 rpm., and the quantity of arphamenine as produced was examined with the passage of time. The production of arphamenine reached a maximum at the end of 32 hours of cultivation. After 36 hours of cultivation, the potency of arphamenine gradually decreased, when evaluated in term of the anti-aminopeptidase B activity of the incubated culture medium. The pH of the incubated culture medium during cultivation changed from 7.4 at the start of cultivation, via 7.8 at 8 hours, 7.6 at 16 hours, 7.85 at 24 hours, 8.1 at 32 hours, 8.1 at 36 hours, and to 8.45 at 52 hours of cultivation.

Example 2

The arphamenine-producing strain, Chromobacterium violaceum BMG361-CF4, was cultivated under the same conditions using the same culture medium as in Example 1. 9.5 Liters of the culture medium after cultivation was adjusted to a pH of 2 with hydrochloric acid, and suction-filtered with a filter aid (Hyflo Super Cell) to obtain 9 liters of the culture broth filtrate. This filtrate had an antiaminopeptidase B potency ($IC_{50}$) of 0.05 $\mu$l/ml.

Example 3

The culture broth filtrate (9 l) obtained in the Example 2 as above was adjusted to a pH of 5 with sodium hydroxide, and adsorbed to a column of 1 l of Amberlite XAD-4. The Amberlite column was washed with water, and then eluted with 50% aqueous acetone. The active fraction (2.3 l) was concentrated to dryness under reduced pressure to obtain 19.6 g of a crude powder. This crude powder showed an anti-aminopeptidase B potency ($IC_{50}$) of 0.2 $\mu$g/ml. Then, the crude powder was dissolved in a suitable volume of a 0.05 M aqueous sodium chloride, and adsorbed to a column of 500 ml of CM-Sephadex C-25 (a product of Sephadex Fine Chemical Co., Sweden). The CM-Sephadex C-25 column was washed with 1.5 liters of a 0.05 M aqueous sodium chloride and with 1 liter of 0.05 M citrate buffer solution (pH 4.5), and then subjected to gradient elution with 2.5 liters of the same buffer solution along with 2.5 liters of the same buffer solution containing 0.55 M sodium chloride. Through this elution procedure, the eluate was collected in 18 ml-fractions. Arphamenine A was obtained in Fraction Nos. 39 to 59, while arphamenine B was obtained in Fraction Nos. 60 to 89. These active fractions were desalted with Amberlite XAD-4, respectively, and then freeze-dried. A crude powder of arphamenine A powder (of an anti-aminopeptidase B potency, $IC_{50}=0.0065$ $\mu$g/ml) was obtained from the arphamenine A fractions in a yield of 188 mg. From the arphamenine B fractions was obtained a crude powder of arphamenine B in a yield of 79 mg (of an anti-aminopeptidase B potency, $IC_{50}=0.0023$ $\mu$g/ml).

Example 4

The crude powder of arphamenine A (188 mg) obtained in Example 3 was dissolved in a suitable volume of 0.05 M aqueous sodium chloride, and the solution was adjusted to a pH of 2.3 with 1 N hydrochloric acid. The solution was adsorbed to an 80 ml column of CM-Sephadex C-25, and this column was washed with 100 ml of 0.07 M aqueous sodium chloride. The CM-Sephadex C-25 column containing the adsorbate was then subjected to gradient elution using 300 ml of 0.07 M aqueous sodium chloride and 300 ml of 0.5 M aqueous sodium chloride. During this purification step, the eluate was collected in 8 ml-fractions, and arphamenine A was eluted out in Fraction Nos. 11 to 34. The Fraction Nos. 11 to 30 were concentrated and adjusted to a pH of 2.3 with 1 N hydrochloric acid. The concentrated solution was desalted by passing through a 500 ml column of Sephadex LH-20, followed by the elution with water. The desalted solution of arphamenine A so obtained was adjusted to a pH of 5 with Dowex WGR resin, and then freeze-dried to obtain 94 mg of arphamenine A as a colorless, pure powder (of an anti-aminopeptidase B potency, $IC_{50}=0.0054$ μg/ml).

Example 5

The crude powder of arphamenine B (79 mg) obtained in Example 3 was dissolved in a suitable volume of 0.05 M aqueous sodium chloride. The solution was adjusted to a pH of 2.3 with 1 N hydrochloric acid and then adsorbed to a 100 ml column of CM-Sephadex C-25. The CM-Sephadex C-25 column containing the adsorbate was washed with 100 ml of 0.15 M aqueous sodium chloride, and then subjected to gradient elution using 350 ml of 0.15 M aqueous sodium chloride and 350 ml of 0.6 M aqueous sodium chloride. During this purification step, the eluate was collected in 11 ml-fractions, and arphamenine B was eluted out in Fraction Nos. 17 to 30. These fractions were concentrated, and the concentrated solution was desalted by passing through a 500 ml column of Sephadex LH-20, followed by the elution with 0.01 N hydrochloric acid. The desalted fraction of arphamenine B so obtained was adjusted to a pH of 5 with Dowex WGR resin, and then freeze-dried to afford 32 mg of arphamenine B as a colorless, pure powder. This arphamenine B product had an anti-aminopeptidase B potency, $IC_{50}=0.0020$ pg/ml.

Example 6

A 500-ml Sakaguchi flask was charged with 80 ml of a culture medium comprising 1.5% glycerin, 1.5% soluble starch, 0.5% Prorich, 1.5% fish meal, 0.2% calcium carbonate and 0.05% anti-foaming agent. The culture medium in the flask was sterilized for 15 minutes at 120° C., cooled, and inoculated with a loopful quantity of a slant culture of *Chromobacterium violaceum* BMG361-CF4 (FERM P-6521 or FERM BF-286). The inoculated culture medium was incubated at 28° C. for 24 hours under shaking at 135 reciprocations per minute to prepare a primary inoculum.

A 100-liter fermentation tank was charged with 50 liters of a culture medium comprising 1.5% glycerin, 1.5% soluble starch, and 0.5% Prorich, 1.74% bonito extract, 0.2% calcium carbonate and 0.05% anti-foaming agent. The culture medium in the tank was sterilized at 120° C. for 30 minutes, cooled, and inoculated with 80 ml of the primary inoculum. The inoculated medium was cultivated for 24 hours at 28° C. with stirring at 200 rpm, while feeding sterilized air at a rate of 50 liters per minute, whereby a secondary inoculum was prepared.

A culture medium (300 l) comprising 3.0% soluble starch, 0.5% Prorich, 1.2% corn gluten meal, 0.2% calcium carbonate and 0.05% anti-foaming agent was put in a 570-liter fermentation tank. The culture medium in the tank was sterilized at 120° C. for 30 minutes, cooled and inoculated with 6 liters of the secondary inoculum. The inoculated culture medium was incubated at 28° C. for 24 hours with stirring at 190 rpm., while feeding 300 liters of air per minute. After cultivation, the culture broth was adjusted to a pH of 2 with sulfuric acid, and suction-filtered using a filter aid (Hyflo Super Cell). The culture broth filtrate was adjusted to a pH of 6 with sodium hydroxide, and suction-filtered again to obtain 185 liters of a filtrate. This filtrate had an antiaminopeptidase B potency, $IC_{50}=0.17$ μl/ml.

10 Liters of carbon for chromatography was added to 185 liters of said filtrate, and the mixture was stirred for 2 hours. The carbon was separated from the mixture by passing through a 200-mesh sieve. The carbon was then washed with 50 liters of water, and admixed with 80 liters of 50% aqueous acetone which had been adjusted to a pH of 2 with hydrochloric acid. The admixture was stirred for 2 hours to extract arphamenine into the aqueous acetone. The carbon was removed from the liquid phase by means of a basket centrifuge, and the extract was concentrated to obtain 3.54 liters of a concentrated solution. The antiaminopeptidase B potency, (IC50) of the concentrated solution was 0.0063 μl/ml.

Example 7

The concentrated solution (3.54 l) obtained in Example 6 was neutralized with 2 N aqueous sodium hydroxide to make 5.35 liters of the solution. The solution was adsorbed to a 1.7-liter column of Amberlite XAD-4 resin and this resin column was washed with water. The column was eluted with 12 liters of 50% aqueous acetone, and 7 liters of the active fraction was concentrated under reduced pressure to yield 280 ml of a concentrated solution. This concentrated solution showed an anti-aminopeptidase B potency ($IC_{50}$) of 0.01 μl/ml. Then, the concentrated solution was adsorbed to a 1.7-liter column of CM-Sephadex C-25, and the CM-Sephadex column was washed with 6 liters of 0.05 M aqueous sodium chloride and with 2 liters of 0.05 M citrate buffer solution (pH 4.5). The washed CM-Sephadex column containing the adsorbate was gradiently eluted with 6 liters of the same citrate buffer solution and 6 liters of the same citrate buffer solution but containing 0.6 M sodium chloride. During this gradient-elution procedure, the eluate was collected in 200 ml fractions. Arphamenine A appeared in Fraction Nos. 30 to 39, and arphamenine B in Fraction Nos. 42 to 52. These active fractions were concentrated and desalted with Amberlite XAD-4 resin, respectively to obtain 85 ml of an arphamenine A fraction ($IC_{50}=0.00058$ μl/ml for antiaminopeptidase B potency) and 43 ml of an arphamenine B fraction ($IC_{50}=0.00031$ μl/ml for anti-aminopeptidase B potency).

Example 8

The arphamenine A fraction (85 ml) obtained in Example 7 was adsorbed to a 240-ml column of an adsorbent, Biogel P-2 (a product of Bio-Rad Company). This adsorbent column was washed with 2.5 liters of water and with 1 liter of 20% aqueous methanol, and eluted with 0.001 M aqueous sodium chloride. The eluate was collected in 18 ml-fractions. Arphamenine A appeared in Fraction Nos. 7 to 1. These active fractions were concentrated, desalted with Amberlite XAD-4, and freeze-dried to afford 1.48 g of arphamenine A as a light yellow powder. This powder showed an anti-aminopeptidase B potency ($IC_{50}$) of 0.030 μl/ml.

Example 9

The arphamenine B fraction (43 ml) obtained in Example 7 was adsorbed to a 240-ml column of an adsorbent, Biogel P-2 (bio-Rad's product). This adsorbent column was washed with 2 liters of water and with 1 liter of 20% aqueous methanol, followed by eluting it with a 0.005 M aqueous sodium chloride. The eluate was collected in 18 ml-fractions, and arphamenine B appeared in Fraction Nos. 6 to 25. These active fractions were concentrated, desalted with Amberlite XAD-4 resin, and freeze-dried. Thereby was obtained 1.89 g of arphamenine B as a light yellow powder which showed an anti-aminopeptidase B potency (IC$_{50}$) of 0.019 μl/ml.

What we claim is:

1. A process for the production of arphamenine A and arphameniine B of the formula

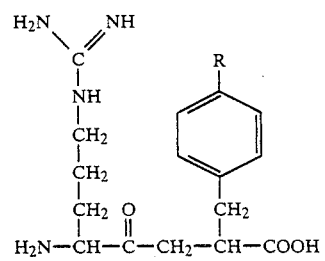

wherein R denotes a hydrogen atom for arophamenine A; and R denotes a hydroxyl group for arphamenine B, which comprises cultivating under aerobic conditions the microorganism Chromobacterium violaceum BMG361-CF4, a strain identified as FERM BP-286 and ATTC 39373, in a culture medium containing assimilable carbon and nitrogen sources for a sufficient time to produce and accumulate arphamenines A and B in the culture medium and recovering armphamenine A and B from said culture medium.

2. A process as claimed in claim 1 in which chromobacterium viilaceum BMG361-CF4 is cultivated at a temperature of 25 to 35? C. for 8 hours to 52 hours.

* * * * *